United States Patent
Van Heesch et al.

(10) Patent No.: US 11,413,021 B2
(45) Date of Patent: Aug. 16, 2022

(54) URINE TURBIDITY MONITORING

(71) Applicant: KONINKLIJKE PHILIPS N.V., Eindhoven (NL)

(72) Inventors: Franciscus Hendrikus Van Heesch, Eindhoven (NL); Igor Wilhelmus Franciscus Paulussen, Nuenen (NL); Nico Maris Adriaan De Wild, Eindhoven (NL); Katia Donato, Copenhagen (DK); Christianus Martinus Van Heesch, Eindhoven (NL); Rick Bezemer, Amsterdam (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 245 days.

(21) Appl. No.: 16/500,145

(22) PCT Filed: Mar. 29, 2018

(86) PCT No.: PCT/EP2018/058265
§ 371 (c)(1),
(2) Date: Oct. 2, 2019

(87) PCT Pub. No.: WO2018/185021
PCT Pub. Date: Oct. 11, 2018

(65) Prior Publication Data
US 2021/0100532 A1    Apr. 8, 2021

(30) Foreign Application Priority Data

Apr. 3, 2017  (EP) .................................... 17164540
May 3, 2017  (EP) .................................... 17169166

(51) Int. Cl.
*A61B 8/00*       (2006.01)
*G16H 40/67*    (2018.01)
(Continued)

(52) U.S. Cl.
CPC ............... *A61B 8/54* (2013.01); *A61B 8/085* (2013.01); *A61B 8/14* (2013.01); *A61B 8/4227* (2013.01);
(Continued)

(58) Field of Classification Search
CPC ............... A61B 8/4245; A61B 8/4488; A61B 8/4227–4236; A61B 8/085
See application file for complete search history.

(56) References Cited

U.S. PATENT DOCUMENTS 4,926,871 A  *  5/1990  Ganguly ................ A61B 5/204
                                                              600/443
5,235,985 A  *  8/1993  Me ......................... A61B 5/204
                                                              128/916
(Continued)

FOREIGN PATENT DOCUMENTS

EP       2989985 A1    3/2016
JP       2016093209 A  5/2016
(Continued)

OTHER PUBLICATIONS

P. K. Verma et al., "Broadband Measurements of the Frequency Dependence of Attenuation Coefficient and Velocity in Amniotic Fluid, Urine and Human Serum Albumin Solutions," Ultrasound in Medicine & Biology, vol. 31, No. 10, pp. 1375-1381, Jun. 2005. (Year: 2005).*
(Continued)

*Primary Examiner* — Oommen Jacob
*Assistant Examiner* — Nyrobi Celestine

(57) ABSTRACT

A wearable bladder monitoring device is disclosed and includes a fastener for securing the device to a subject's body; a phased array of ultrasound transducers having configurable output frequencies; a configurable phased array controller adapted to control the phased array to direct
(Continued)

ultrasound beams into the subject's body under a plurality of discrete beam angles and to collect echo signals of the ultrasound beams, wherein the phased array controller is adapted to direct a set of ultrasound beams into the subject's body for at least a subset of the discrete beam angles in response to a configuration instruction defining the respective output frequencies of the ultrasound beams in the set; and a device transceiver for communicating data pertaining to the echo signals to a remote device to facilitate the remote processing of the data and to receive the configuration instruction from the remote device.

20 Claims, 10 Drawing Sheets

(51) Int. Cl.
  *G16H 50/30* (2018.01)
  *A61B 8/08* (2006.01)
  *A61B 8/14* (2006.01)
(52) U.S. Cl.
  CPC .......... *A61B 8/4236* (2013.01); *A61B 8/4245* (2013.01); *A61B 8/4472* (2013.01); *A61B 8/4488* (2013.01); *A61B 8/5223* (2013.01); *A61B 8/56* (2013.01); *G16H 40/67* (2018.01); *G16H 50/30* (2018.01)

(56) References Cited

U.S. PATENT DOCUMENTS

| | | | | |
|---|---|---|---|---|
| 5,964,710 | A * | 10/1999 | Ganguly | A61B 8/0858 |
| | | | | 600/449 |
| 6,359,190 | B1 * | 3/2002 | Ter-Ovanesyan | A61L 15/18 |
| | | | | 604/361 |
| 6,406,431 | B1 | 6/2002 | Barnard et al. | |
| 8,221,321 | B2 * | 7/2012 | Me | A61B 8/4455 |
| | | | | 600/437 |
| 9,492,113 | B2 * | 11/2016 | Nagale | A61B 5/205 |
| 9,713,459 | B2 * | 7/2017 | Mattrey | A61K 49/223 |
| 2006/0276707 | A1 | 12/2006 | Ya'akov et al. | |
| 2008/0139934 | A1 * | 6/2008 | Me | A61B 8/0858 |
| | | | | 600/438 |
| 2008/0281322 | A1 * | 11/2008 | Sherman | A61B 18/1206 |
| | | | | 606/42 |
| 2010/0016763 | A1 | 1/2010 | Keilman | |
| 2010/0160784 | A1 * | 6/2010 | Poland | A61B 8/00 |
| | | | | 600/453 |
| 2010/0198075 | A1 | 8/2010 | McMorrow et al. | |
| 2013/0178742 | A1 * | 7/2013 | Kristiansen | A61B 8/0858 |
| | | | | 600/449 |
| 2016/0058411 | A1 * | 3/2016 | Yoshimura | A61B 8/5223 |
| | | | | 600/438 |
| 2019/0350553 | A1 * | 11/2019 | Pop | A61B 8/4416 |

FOREIGN PATENT DOCUMENTS

| | | |
|---|---|---|
| WO | 2002094089 A2 | 11/2002 |
| WO | 2005034717 A2 | 4/2005 |
| WO | 2016085341 A1 | 6/2016 |
| WO | 2016118943 A2 | 7/2016 |

OTHER PUBLICATIONS

K. Van den Bussche et al., "Urinary Mineral Concentrations in European Pre-Adolescent Children and Their Association with Calcaneal Bone Quantitative Ultrasound Measurements," International Journal of Environmental Research and Public Health, vol. 13, No. 5, pp. 1-17, May 2016. (Year: 2016).*
International Search Report and Written Opinion, International Application No. PCT/EP2018/058265, dated May 28, 2018.
"Lumify: Exceptional portable ultrasound machine on your smartphones and handheld devices", Philips, https://www.usa.philips.com/healthcare/sites/lumify, Accessed Sep. 27, 2019.
Verathon, http://www.verathon.nl/bladderscan/, Accessed Sep. 27, 2019.

* cited by examiner

URINE TURBIDITY MONITORING

CROSS-REFERENCE TO PRIOR APPLICATIONS

This application is the U.S. National Phase application under 35 U.S.C. § 371 of International Application No. PCT/EP2018/058265, filed on 29 Mar. 2018, which claims the benefit of European Patent Application Numbers 17164540.1, filed on 3 Apr. 2017 and 17169166.0, filed on 3 May 2017. These applications are hereby incorporated by reference herein.

FIELD OF THE INVENTION

The present invention relates to a bladder monitoring device for monitoring urine turbidity, a bladder monitoring system comprising such a bladder monitoring device, a method of monitoring turbidity of urine contained within a bladder with such a system and a computer program product for implementing such a method on a bladder monitoring system.

BACKGROUND OF THE INVENTION

In medicine, there is an on-going interest in monitoring the bladder volume of a subject, e.g. a patient. As is well-known per se, the bladder is a triangularly shaped hollow organ for storing urine, with elastic walls such that the bladder can expand upon receiving urine from the kidneys before expelling the urine through the subject's urethra.

There are a number of reasons why such bladder volume monitoring is of interest. For example, the bladder retention volume (i.e. the amount of urine retained by the bladder after the subject's urinating) is an indicator of prostate and urinary tract conditions, which conditions may be triggered by bacteria and other pathogens in the retained urine. In particular, the turbidity of the retained urine provides an important indicator of such conditions. Consequent bladder stretching is a key contributor to the occurrence of delirium in elderly subjects; the bladder filling rate is an indicator for the hydration state and kidney function of the subject, and so on.

US 2010/0016763 A1 discloses an intraluminal fluid property status sensing system that locates an acoustic transducer within a lumen of a biological creature to transmit ultrasound through intraluminal fluid to be reflected or otherwise affected by the fluid with subsequent reception by the same transducer. Reflection or interaction of the ultrasound with an intraluminal fluid depends upon one or more properties of the intraluminal fluid such that it can be used to determine the status of such properties. In a particular example, the concentration of cells or electrolytes in urine is determined from a difference in attenuation of two or more ultrasound echo signals measured at different distance ranges, which attenuation increases with ultrasonic signal frequency.

However, such a system requires permanent or temporary implanting into the subject, which is stressful to the patient and increases the risk of infections resulting from the implanting procedure.

SUMMARY OF THE INVENTION

The present invention seeks to provide a bladder monitoring system for controlling a bladder monitoring device in response to ultrasound echo data produced by the bladder monitoring device.

The present invention further seeks to provide a computer-implemented method for determining a degree of turbidity of urine contained in the bladder of a subject monitored with such a wearable bladder monitoring device.

The present invention further seeks to provide a computer program product for implementing such a method on a bladder monitoring system.

Embodiments of the present invention utilize a wearable bladder monitoring device comprising securing means for securing the device to a subject's body; a phased array of ultrasound transducers having configurable output frequencies; a configurable phased array controller adapted to control the phased array to direct ultrasound beams into the subject's body under a plurality of discrete beam angles and to collect echo signals of said ultrasound beams, wherein the phased array controller is adapted to direct a set of ultrasound beams into the subject's body for at least a subset of said discrete beam angles in response to a configuration instruction defining the respective output frequencies of the ultrasound beams in said set; and a device communication module for communicating data pertaining to said echo signals to a remote device to facilitate the remote processing of said data and to receive said configuration instruction from the remote device.

Such a wearable bladder monitoring device facilitates the determination of urine turbidity by a bladder monitoring system by virtue of the configurability of the phased array controller and the output frequency of the ultrasound transducers of the phased array, i.e. the ultrasound frequency of the ultrasound beams produced by these ultrasound transducers, such that upon processing of the data pertaining to the echo signals of the ultrasound beams under the different discrete angles into the subject's body, the positioning and volume of the subject's bladder relative to the position of the wearable bladder monitoring device on the subject's body can be derived from this data by the bladder monitoring system, from which the bladder monitoring system can define one or more ultrasound beams of defined ultrasound frequencies to be generated with the phased array of ultrasound transducers in the form of a configuration instruction for the configurable phased array controller, which defined ultrasound frequencies are defined such that the bladder monitoring system can estimate a degree of turbidity of the urine contained within the subject's bladder from the data pertaining to the echo signals of these defined one or more ultrasound beams. In this manner, a bladder monitoring device is provided that can be used in a non-invasive manner in conjunction with a remote device, i.e. the bladder monitoring system, in order to monitor the subject's bladder and to obtain bladder information such as bladder volume, changes in bladder volume and degree of turbidity of the urine contained within the bladder in a non-invasive manner.

The phased array controller may be further configurable to operate the phased array at an operating frequency defined by a monitoring instruction received through the device communication module. Such operating frequency, i.e. the frequency at which the bladder monitoring device monitors the bladder, for example may be defined by the bladder monitoring system based on a monitored rate of change of the bladder volume, such that the operating frequency may be optimized, e.g. to extend battery life of the wearable bladder monitoring device, whilst minimising the risk that the operating frequency is chosen such that a critical value of the bladder volume may be missed, such as for example a critical value indicative of the subject need to pass urine, as the detection of such a critical value may be used to warn the subject accordingly. Such a warning may be used by the subject to pass urine, for example to avoid involuntary passing of urine in case of incontinence.

In order to facilitate communication between the wearable bladder monitoring device and a remote device as previously explained, the wearable bladder monitoring device may further comprise a wireless communication module for communicating a processing result of the data processor to a remote device or to communicate (pre-processed) echo signals to a data processor of such a remote device.

The securing means may include a strap attached to the wearable bladder monitoring device or an adhesive layer on a subject-facing surface of the wearable bladder monitoring device. The adhesive layer is particularly preferred as this is capable of securely fastening the wearable bladder monitoring device with minimal risk of the device accidentally moving into another location relative to the subject's bladder, and has the further advantage of being minimally intrusive compared to the strap, which may be perceived as less comfortable at least by some users.

According to an aspect of the present invention, there is provided a bladder monitoring system for processing the data pertaining to the echo signals from such a wearable bladder monitoring device, the system comprising a system communication module for receiving data pertaining to echo signals from the device communication module of the wearable bladder monitoring device; and a data processor communicatively coupled to the system communication module and adapted to process the data pertaining to the echo signals to identify an edge of the subject's pelvic bone proximal to the subject's bladder from data pertaining to at least one of said echo signals; determine an orientation of the wearable bladder monitoring device relative to the pelvic bone based on beam angle information associated with at least one of said echo signals; and derive bladder information from the data based on the determined orientation; the data processor further being arranged to generate a configuration instruction defining a set of output frequencies for at least a subset of said discrete beam angles based on said defined bladder information for determining a degree of turbidity of urine contained in said bladder, said configuration instruction causing the configurable phased array controller to generate a set of ultrasound beams each having a defined output frequency of said set of output frequencies for each of the discrete beam angles in said subset; and control the system communication module to communicate the configuration instruction to the device communication module of the wearable bladder monitoring device.

Particular aspects of the present invention are based on the insight that the position and/or orientation of the wearable bladder monitoring device relative to the bladder can be variable and that moreover the distance of the phased array of ultrasound transducers to the bladder typically is a function of this position and/or orientation as well as of the actual volume of the bladder being monitored. More specifically, the present invention is based on the insight that by generating a plurality of ultrasound beams under a range of beam angles with such a phased array, the echoes of such ultrasound beams can be categorized into three distinguishable categories, namely a first category of echoes incident on the pelvic bone, a second category of echoes passing through the bladder and a third category of echoes passing through tissue adjacent to the bladder. In this manner, based on the beam angle information the orientation of the wearable bladder monitoring device relative to the pelvic bone can be retrieved from the echoes, which orientation can be used to accurately estimate the bladder volume from the subset of echoes relating to ultrasound beams passing through the bladder, which echoes may be further sub-categorized in echoes passing through the bladder wall and echoes passing through urine in the bladder.

Consequently, in order to facilitate an accurate estimation of the degree of turbidity of urine contained in the monitored bladder, the output frequency of the ultrasound beams generated with the phased array of ultrasound transducers needs to be optimized as a function of these variables. Hence, the data processor of the bladder monitoring system typically is configured to process data pertaining to echo signals of ultrasound beams having an initial output frequency as received from the bladder monitoring device from which these variables can be determined, which information is subsequently used to define a set of output frequencies, i.e. one or more output frequencies, for a subset of the discrete beam angles, typically the beam angles under which ultrasound beams pass through the bladder, which set of output frequencies is optimized as a function of the determined variables for the determination of the degree of turbidity of urine contained within the monitored bladder from data pertaining to the echo signals of the ultrasound beams generated in accordance with the set of output frequencies.

The set of ultrasound frequencies may comprise a first set of ultrasound frequencies for a first discrete beam angle in said subset and a second set of ultrasound frequencies for a second discrete beam angle in said subset. In this manner, each set of ultrasound beams to be generated under a particular beam angle may have individually optimized output frequencies for that particular beam angle, thus further increasing the accuracy of the estimation of the degree of turbidity of urine contained within the monitored bladder.

Preferably, the data processor is further adapted to determine said degree of turbidity from the data pertaining to the echo signals of the set of ultrasound beams such that the bladder monitoring system not only controls the generation of the optimized frequency ultrasound beams by the generation of the aforementioned configuration instruction but furthermore processes the echo signals of the optimized frequency ultrasound beams and estimates the degree of turbidity of the urine contained within the monitored bladder. In an embodiment, the data processor is adapted to determine at least one particle size of a substance and a concentration of a substance in the urine contained in the bladder of the subject based on a frequency-dependent attenuation of the echo signals of the set of ultrasound beams. Particular aspects of the present invention are based on the insight that particle size and concentration can be derived from such frequency-dependent attenuation, which may provide further insights as to which type of substance is contained within urine, as different types of substances are typically characterised by different particle sizes.

The data processor may be adapted to estimate a diameter of the subject's bladder for each echo signal from the data pertaining to the echo signals of the ultrasound beams and to estimate a bladder volume by fitting the estimated diameters of the subject's bladder to a defined bladder model and estimating the bladder volume from the fitting result. This is a particularly straightforward manner of obtaining an estimate of the monitored bladder volume. In the context of the present application, the term 'diameter' is used to refer to a cross-sectional length or width of the bladder between opposing bladder wall sections through which the ultrasound beam responsible for the echo signal propagates.

The data processor further may be adapted to generate the configuration instruction in response to the estimated bladder volume at least matching a defined minimum value. In this manner, it for example can be ensured that a urine turbidity measurement is only performed once there is sufficient urine retained within the monitored bladder to facilitate such a measurement.

The data processor further may be adapted to define an operating frequency of the bladder monitoring device based on a determined rate of change in the estimated bladder volume and to generate a monitoring instruction for the wearable bladder monitoring device based on the defined operating frequency. As previously explained, this may be used to extend the battery life of the wearable bladder monitoring device.

According to another aspect, there is provided a computer-implemented method for determining a degree of turbidity of urine contained in the bladder of a subject monitored with the wearable bladder monitoring device of any of the herein described embodiments, the method comprising receiving the data pertaining to said echo signals from the device communication module; processing the data pertaining to the echo signals to identify an edge of the subject's pelvic bone proximal to the subject's bladder from data pertaining to at least one of said echo signals; determine an orientation of the wearable bladder monitoring device relative to the pelvic bone based on beam angle information associated with the at least one of said echo signals; and derive bladder information from the data based on the determined orientation; generating a configuration instruction defining a set of output frequencies for at least a subset of said discrete beam angles based on said defined bladder information for determining a degree of turbidity of urine contained in said bladder, said configuration instruction causing the configurable phased array controller to generate a set of ultrasound beams each having a defined output frequency of said set of output frequencies for each of the discrete beam angles in said subset; and communicating the configuration instruction to the device communication module of the wearable bladder monitoring device.

Such a method may for example be implemented by the bladder monitoring system of the present invention in order to facilitate the accurate estimation of urine turbidity within the monitored bladder as previously explained.

The computer-implemented method preferably further comprises determining said degree of turbidity from the data pertaining to the echo signals of the set of ultrasound beams.

In an embodiment, the computer-implemented method further comprises determining at least one of a particle size of at least one substance and a concentration of at least one substance in the urine contained in the bladder of the subject based on a frequency-dependent attenuation of the echo signals of the set of ultrasound beams in order to determine the nature and/or concentration of the substance(s) in the urine contained within the monitored bladder, which may provide important clinical information based on which specific medical conditions may be diagnosed.

According to another aspect, there is provided a computer readable storage medium having computer readable program instructions embodied therewith for, when executed on a data processor of the bladder monitoring system of any of the herein described embodiments, cause the data processor to implement the method of any of the herein described embodiments. Such a computer readable storage medium may be accessed by the data processor of such a bladder monitoring system to implement embodiments of the herein described method.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
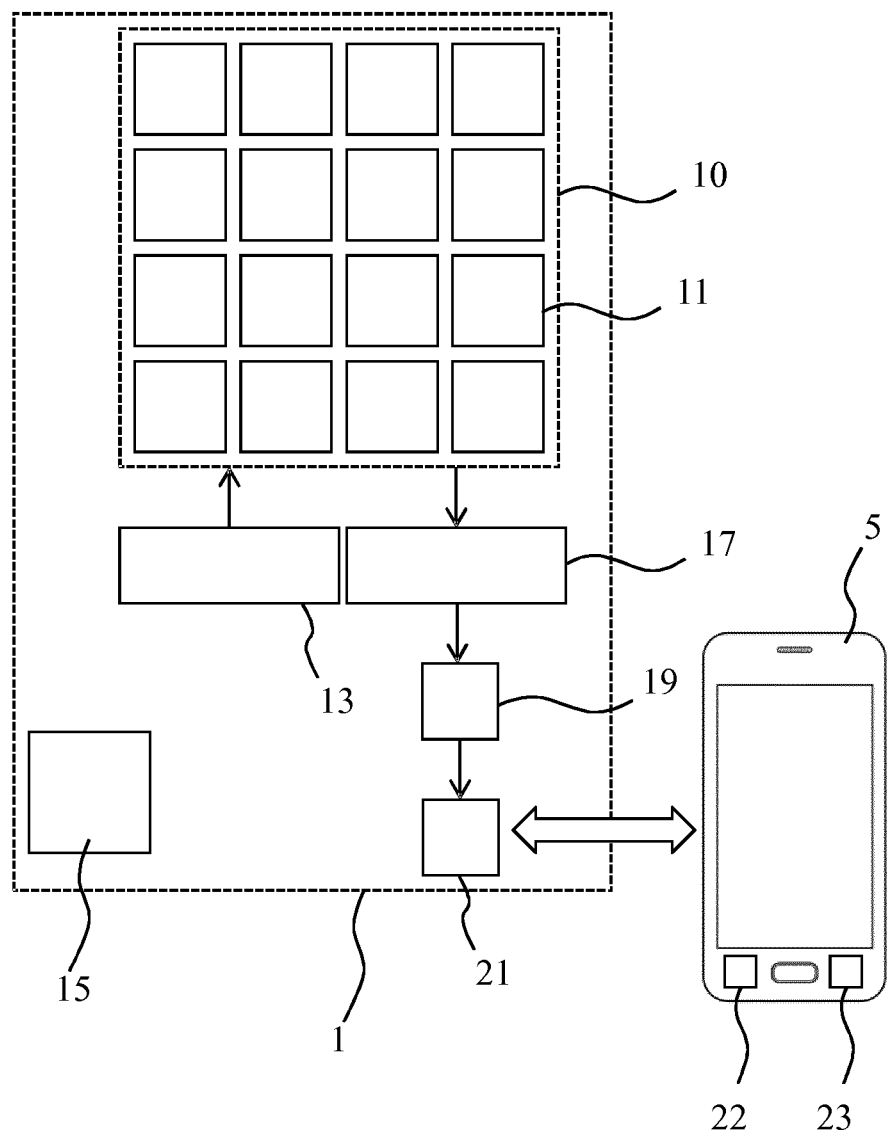
FIG. 1 schematically depicts a bladder monitoring system according to an embodiment.

It should be understood that the Figures are merely schematic and are not drawn to scale. It should also be understood that the same reference numerals are used throughout the Figures to indicate the same or similar parts.

FIG. 1 schematically depicts a bladder monitoring system according to an example embodiment. The bladder monitoring system comprises a wearable bladder monitoring device 1 that may be secured to an individual (subject) using suitable securing means, such as a strap or belt, or an adhesive layer as will be explained in more detail later. The wearable bladder monitoring device 1 comprises a phased array 10 of ultrasound transducer elements 11 under control of a phased array controller 13. Any suitable type of ultrasound transducer elements 11 may be used for this purpose, e.g. PZT elements, CMUT elements, PMUT elements, and so on, although CMUT elements are particularly preferred, in particular over PZT elements due to their superior (adjustable) resonance (output) frequency range, which make CMUT elements particularly suitable for bladder monitoring purposes. As such transducer elements are well-known per se, they will not be explained in further detail for the sake of brevity only.

The phased array 10 may take any suitable shape, e.g. a one-dimensional array or two-dimensional array of ultrasound transducer elements 11 of any suitable size, such as a 4×4 mm array 10 having 16 ultrasound transducer elements 11 with a pitch in a range of 200-300 microns, by way of non-limiting example. Other dimensions are of course equally feasible. In an embodiment, the ultrasound transducer elements 11 are operable in a frequency range of 2-12 MHz, although other frequency ranges may be contemplated. As will be explained in more detail below, the operation or output frequency of the ultrasound transducer elements 11 may be altered under control of a phased array controller 13.

Figure 2:
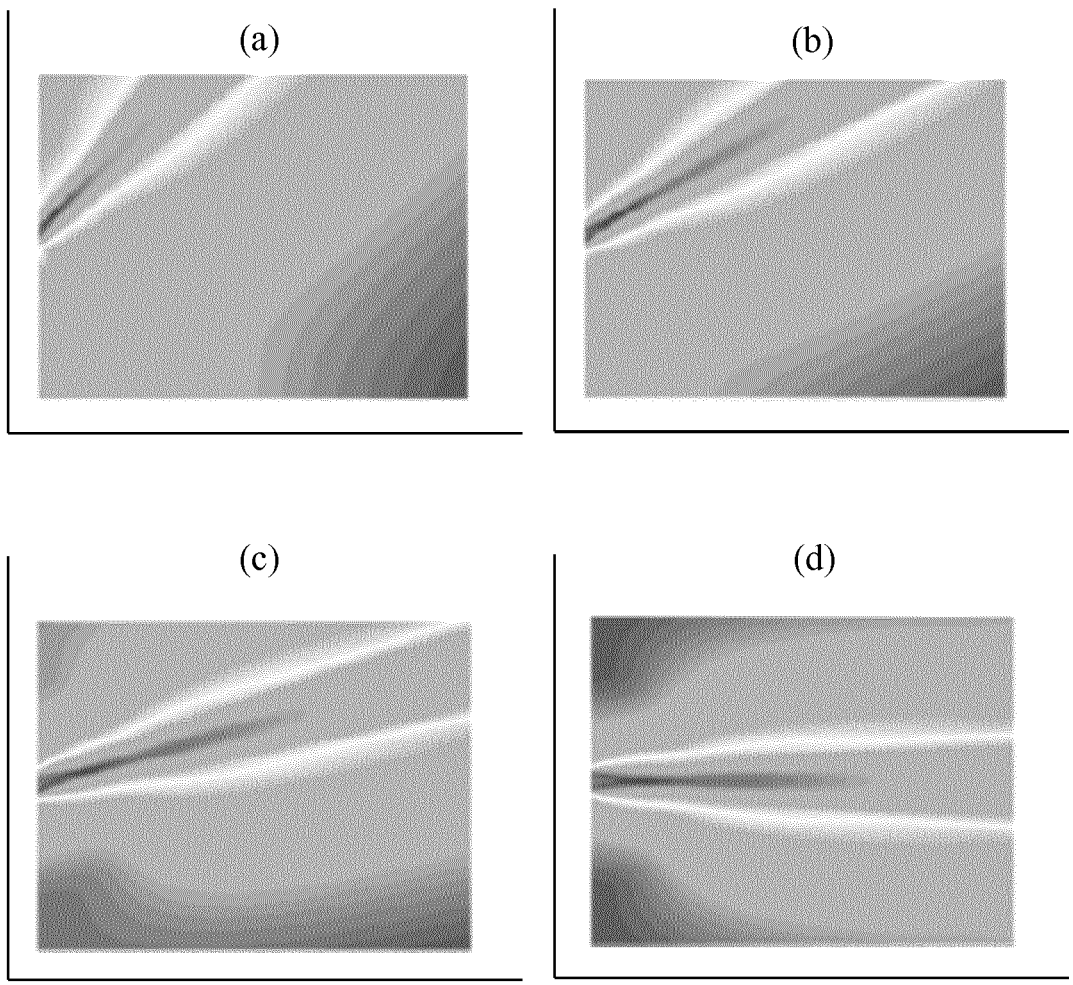
FIG. 2 schematically depicts an operating principle of a bladder monitoring system according to an embodiment.

The phased array controller 13 typically is arranged to steer ultrasound beams generated with the ultrasound transducer elements 11 of the phased array 10 under a range of angles, as schematically depicted in FIG. 2, in which by varying the delay times between the firing of the individual (lines of) ultrasound transducer elements 11 as is well-known per se, beams may be generated under a number of beam angles, e.g. 45° (a), 30° (b), 15° (c) and 0° (d), wherein the beam angle is defined relative to the transmission surface of the phased array 10. In an embodiment, the beam angle range ranges from 0° to 45°, in which beam angles are altered in 15° increments, although a larger or smaller beam angle range utilizing larger or smaller beam angle increments of course may also be contemplated.

As will be explained in more detail below, the phased array controller 13 may be configured by a configuration instruction, which causes the phased array controller 13 to control the phased array 10 such that its transducer elements 11 generate a set of ultrasound beams under a selection of the full range of discrete beam angles as defined by the configuration instruction, with the configuration instruction further defining the ultrasound frequency of each of these ultrasound beams. Typically, where such a set of ultrasound beams contains more than one ultrasound beam to be generated under a particular beam angle, these ultrasound beams will have different ultrasound frequencies as defined by the configuration instruction.

Now, upon returning to FIG. 1, the phased array 10 typically is operable in a transmit mode in which the ultrasound beams are generated under control of the phased array controller 13 and a receive mode in which the phased array is operable to receive echo signals induced by the generated ultrasound beams within the body of the individual wearing the wearable bladder monitoring device 1. As will be readily understood by the skilled person, the wearable bladder monitoring device 1 may be operated such that a transmit mode of an ultrasound beam under a particular beam angle is followed by the receive mode of its induced echo signals, before the next transmit mode of an ultrasound beam under a further particular beam angle is initiated, such as to ensure that for each ultrasound beam its echoes do not suffer interference from echoes of ultrasound beams under different beam angles.

The echo signals may be pre-processed by a pre-processing stage 17, which may form part of the phased array controller 13 or may be a separate entity. The pre-processing stage 17 may apply noise filtering and frequency down conversion of the echo signals, e.g. from the MHz domain to the KHz domain, and employ a signal envelope to the down converted echo signals to reduce the amount of data that needs to be provided to a data processor for deriving the desired bladder information from the acquired echo signals. Other suitable data pre-processing techniques will be immediately apparent to the skilled person.

In FIG. 1, the data processor 23 forms part of a remote device 5, e.g. a wearable smart device such as a smart watch, a portable smart device such as a mobile phone or tablet computer, a laptop computer, a personal computer, or the like in order to reduce the computational effort required from the wearable bladder monitoring device 1 such that the lifetime of the battery 15 of the wearable bladder monitoring device 1 may be extended. The remote device 5 may be configured to obtain the desired functionality for the data processor 23 in any suitable manner, e.g. by means of a software program installed onto the remote device 5, such as an app or the like.

To this end, the pre-processing stage 17 may be communicatively coupled to a data storage device 19, e.g. a memory or the like, on-board the wearable bladder monitoring device 1, with a wireless communication module 21 communicatively coupled to the data storage device 19 such that the data pertaining to the acquired echo signals as stored in the data storage device 19 may be communicated at suitable moments to a system communication module 22 of the remote device 5, e.g. in response to a communication request from the remote device. Any suitable wireless communication protocol, e.g. Bluetooth, Wi-Fi, a mobile communication protocol such as 3G, 4G, 5G or the like, a near field communication protocol (NFC), and so on, may be deployed for the communication between the wearable bladder monitoring device 1 and the remote device 5. As mentioned previously, the data pertaining to the acquired echo signals communicated from the wearable bladder monitoring device 1 to the remote device 5 preferably is reduced in size to minimize the amount of data that needs to be communicated in this manner in order to extend the lifetime of the battery 15.

In some embodiments, the remote device 5 may define the bladder monitoring system, with the wearable bladder monitoring device 1 not forming part of this system. In alternative embodiments, the bladder monitoring system includes both the remote device 5 and the wearable bladder monitoring device 1. In another set of embodiments, the data processor 23 is contained within the wearable bladder monitoring device 1. In such embodiments, the wireless communication module 21 may be used to communicate a processing result of the data processor 23 to the remote device 5, e.g. for visualization of the processing result on a display 7 of the remote device 5.

In yet a further embodiment, the wearable bladder monitoring device 1 is configured to upload the data pertaining to the acquired echo signals with a wireless communication module 21 into a remote data repository acting as an intermediary data storage device from which the remote device 5 may download the stored data. This has the advantage that the remote device 5 does not have to be within communication range of the wearable bladder monitoring device 1 but instead may download the data with the system communication module 22 at any suitable point in time to evaluate this data. For example, the remote data repository may be a cloud storage solution or the like, which may be accessed by both the wearable bladder monitoring device 1 and the remote device 5 over a network connection such as the Internet, in which case the wearable bladder monitoring device 1 may establish a wireless connection with an Internet hub such as a router or the like within communication range of the wireless communication module 21 through which the data pertaining to the acquired echo signals may be uploaded into the remote data repository.

Any suitable type of battery 15 may be used within the wearable bladder monitoring device 1. The battery 15 may be non-rechargeable, which for example may be acceptable where the wearable bladder monitoring device 1 is a disposable device. Alternatively, the battery 15 may be a rechargeable battery in which case the wearable bladder monitoring device 1 may comprise a recharging port (not shown) through which the battery 15 may be recharged in any suitable manner. In the absence of such a recharging port, the battery 15 may be recharged using wireless recharging, e.g. NFC recharging as is well-known per se.

Alternatively, the bladder monitoring device 1 may be connected to a remote device 5 through a wired connection for the aforementioned data transfer. In case of such a wired connection, power may be supplied to the bladder monitoring device 1 over the wired connection, in which case the battery 15 may be omitted from the bladder monitoring device 1.

Figure 3:
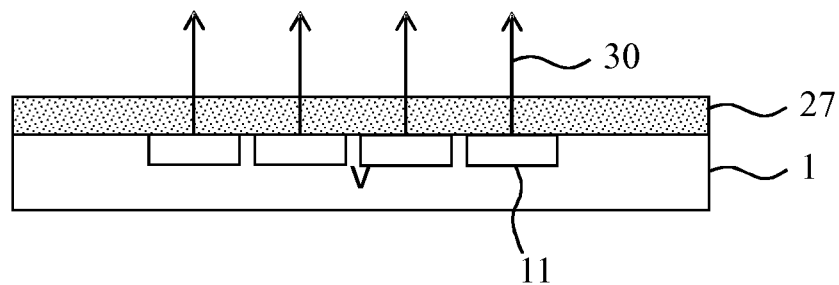
FIG. 3 schematically depicts an aspect of a bladder monitoring system according to an embodiment.

FIG. 3 schematically depicts a cross-section of a wearable bladder monitoring device 1 in which a subject-facing surface of the wearable bladder monitoring device 1 is covered with an adhesive layer 27, e.g. an adhesive polymer layer or the like, for adhering the wearable bladder monitoring device 1 to an abdominal skin region of the subject, such that ultrasound beams 30 originating from the ultrasound transducer elements 11 can be steered into the subject's body under control of the phased array controller 13 as previously explained. The use of an adhesive layer 27 has the advantage of achieving a particularly secure fit between the abdominal skin region of the subject and the wearable bladder monitoring device 1, in particular if no hair is present in this skin region.

Figure 4:
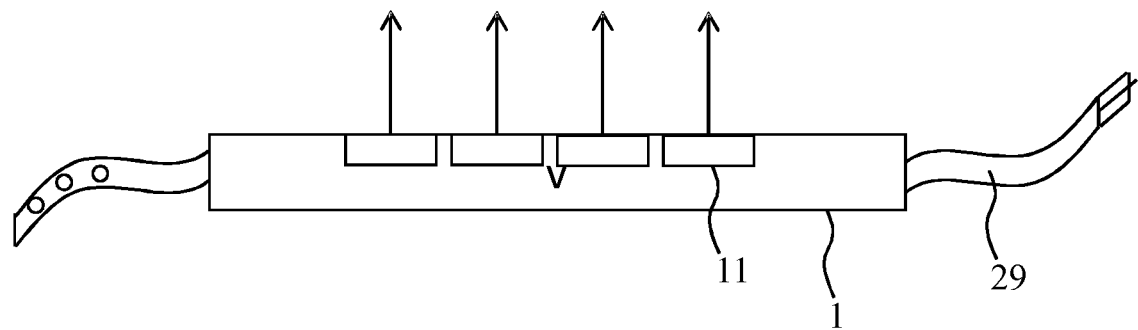
FIG. 4 schematically depicts an aspect of a bladder monitoring system according to another embodiment.

FIG. 4 schematically depicts a cross-section of a wearable bladder monitoring device 1 in which the wearable bladder monitoring device 1 comprises a strap 29 for securing the bladder monitoring device 1 against the abdominal skin region of the subject. Such a strap 29 may be secured against the subject in any suitable manner, e.g. using a fastening member arrangement such as a belt buckle at one end of the strap 29 and holes for receiving the belt buckle at another end of the strap 29, a fastening clip through which the strap 29 can be adjusted in an non-engaged configuration of the clip and in which the strap 29 can be affixed in an engaged configuration of the clip, a Velcro arrangement, and so on. It should furthermore be understood that the strap 29 does not necessarily include a fastening member arrangement; alternatively, the strap 29 may be a closed loop, e.g. a closed belt or the like, which is elastic such that the strap 29 can be stretched to position the wearable bladder monitoring device 1 over the desired abdominal skin region of the subject, such that the elastic force of the stretched elastic strap 29 retains the wearable bladder monitoring device 1 in the desired position and preferably in a preferred orientation. In further embodiments, the wearable bladder monitoring device 1 may have a fastening arrangement in which the adhesive layer 27 is combined with a strap 29 according to any of the aforementioned embodiments.

Figure 5:
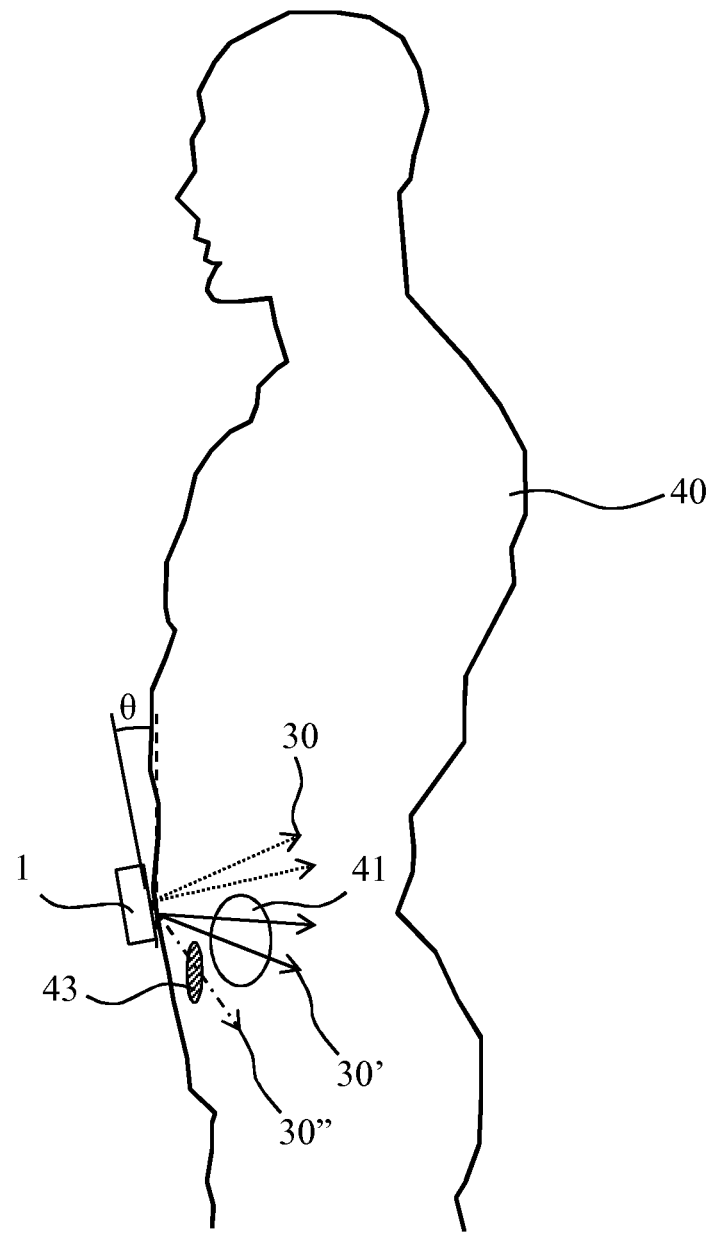
FIG. 5 schematically depicts a bladder monitoring system according to an embodiment in use on a subject.

FIG. 5 schematically depicts the positioning of the wearable bladder monitoring device 1 on the abdominal region of the subject 40. The wearable bladder monitoring device 1 preferably is positioned in an abdominal region in between the pelvic bone 43 and the bellybutton (not shown) of the subject 40, e.g. a few centimetres below the belly button in order to facilitate a good viewing angle of the bladder 41 of the subject 40, i.e. to minimize the area of the bladder 41 that is obscured from direct view of a phased array 10 of ultrasound transducer elements 11. In the context of the present application, such a direct view is a transmission path of an ultrasound beam 30 towards the bladder 41 that does not first have to pass through a skeletal structure such as a bone.

As is schematically depicted in FIG. 5, the beam steering applied by the phased array controller 30 typically results in a plurality of ultrasound beams under a range of beam angles being created, wherein different (subsets of) ultrasound beams travel through different anatomical structures of the subject 40. For example, ultrasound beams 30 as indicated by the finely dashed arrows travel through tissue only, whereas ultrasound beams 30' as indicated by the solid arrows travel through a small layer of tissue before travelling through the bladder 41, whilst ultrasound beams 30" as indicated by the coarsely dashed arrow travelling towards the pelvic bone 43.

Figure 6:
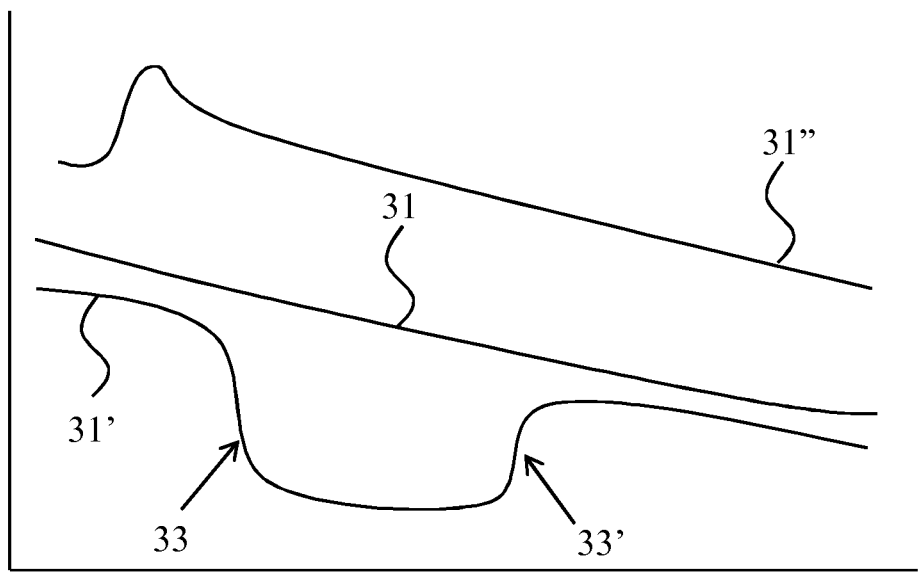
FIG. 6 schematically depicts an aspect of typical echo signals received by a bladder monitoring system according to an embodiment.

An important aspect of embodiments of the present invention is that such different paths of the ultrasound beams 30, 30', 30" lead to clearly distinguishable echo signals, as is schematically depicted in FIG. 6, in which echo signal intensities (y-axis) as a function of time (i.e. object distance from the phased array causing the signal reflection; x-axis) are depicted. Specifically, the ultrasound beams 30 travelling through tissue only typically yield an echo signal 31 having a continually decreasing signal intensity with increasing echo acquisition time delay, whereas the ultrasound beams 30' travelling through the bladder 41 cause echo signals 31' that are characterised by a sudden change 33' in the echo signal intensity, or by a pair of such signal intensity changes 33 and 33', which signal intensity changes are characteristic of the echo signals encountering the anterior wall of the bladder 41 at a first distance from the phased array 10 (signal intensity change 33) and the posterior wall of the bladder 41 at a second distance from the phased array 10 (signal intensity change 33'), with the echo signal in between these respective signal intensity changes indicative of the medium, e.g. urine or tissue, in the bladder 41 in between the anterior and posterior wall portions imaged by the ultrasound beam from which the echo signal 31' has originated. Finally, the echo signal 31" resulting from ultrasound beams 30" incident on the pelvic bone 43 is characterised by a sharp intensity peak caused by the reflection of the ultrasound beams by the pelvic bone 43 at a relatively close distance from the phased array 10.

Figure 7:
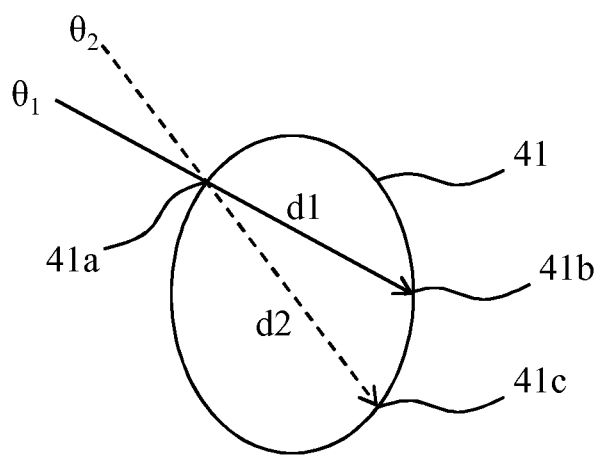
FIG. 7 schematically depicts an angular dependence of ultrasound signals passing through a subject's bladder resulting from orientations of the bladder monitoring system according to an embodiment relative to the subject.

The distance between the intensity changes in an echo signal 31' indicative of the anterior and posterior wall portions imaged by an ultrasound beam 30' from which this echo signal originates may be used to estimate a diameter of a section of the bladder 41, as schematically depicted in FIG. 7, in which an ultrasound beam 30' enters the bladder 41 through anterior wall portion 41a. However, depending on the relative orientation of the wearable bladder monitoring device 1 to the abdominal region of the subject 40, as expressed by the angle θ in FIG. 5, the ultrasound beam 30' may exit the bladder through its posterior wall portion 41b if the wearable bladder monitoring device 1 is oriented relative to the abdominal region of the subject 40 under a first angle $\theta_1$, giving rise to an estimated diameter d1 as being the distance (time delay) between the midpoints of the edges 33 and 33' of the echo signal, which midpoints may be interpreted as the estimated locations of the anterior wall portion 41a and the posterior wall portion 41b.

On the other hand, the ultrasound beam 30' may exit the bladder through its posterior wall portion 41c if the wearable bladder monitoring device 1 is oriented relative to the abdominal region of the subject 40 under a second angle $\theta_2$, giving rise to an estimated bladder diameter d2, with typically d2≠d1. In this context, the angle θ may be defined as the angle between the subject-facing surface plane of the wearable bladder monitoring device 1 and the plane of the abdominal skin contact region onto which the wearable bladder monitoring device 1 is placed. This therefore shows that the relative orientation of the wearable bladder monitoring device 1 to the abdominal region of the subject 40 has an impact on the bladder monitoring data, in particular on the length of a path of an ultrasound beam 30' through a section of the bladder 41 as explained above.

The operation of the bladder monitoring system according to embodiments of the present invention is designed to factor in such orientational dependency of the wearable bladder monitoring device 1 on the bladder monitoring results, as will now be explained in more detail with the aid of FIG. 8, in which a flowchart of a method 100 of monitoring the bladder 41 of a subject 40 with such a bladder monitoring system is shown. The method 100 starts in operation 101 with the placement of the wearable bladder monitoring device 1 in a defined location on the abdomen of the subject 40, e.g. just under the subject's bellybutton as previously explained, after which in operation 103 the phased array controller 13 controls the phased array 10 to generate a plurality of ultrasound beams 30 into the subject's body under a range of beam angles, e.g. a range from 0-45° with defined beam angle increments, e.g. 5° or 15° increments. For each generated ultrasound beam 30, an echo signal 40 is received in operation 105 before the ultrasound beam 30 under the next beam angle is generated in a repeat of operation 103. Any suitable acquisition period for the echo signals 40 may be deployed in operation 105, e.g. an acquisition period of several milliseconds.

Each received echo signal may be pre-processed by the pre-processing state 17 in operation 107, which pre-processing may include one or more or noise filtering, signal enveloping, signal down conversion, and signal digitization, and which may further include storing the pre-processed signal in data storage device 19 for subsequent processing by the data processor 23, either on a remote device 5 or on the wearable bladder monitoring device 1 as previously explained. It is checked in operation 108 if all ultrasound signals 30 under the desired beam angles have been generated, the respective echo signals 40 have been collected and pre-processed. If this is not the case, the method 100 reverts back to operation 103 in which the next ultrasound beam 30 is generated, e.g. under an adjusted beam angle.

Otherwise, the method 100 proceeds to operation 109 in which the acquired (pre-processed) ultrasound echo signals 40 are passed on to the data processor 23, which may involve a wireless communication between the wearable bladder monitoring device 1 and the remote device 5 as previously explained in case the data processor 23 is located on the remote device 5, in which the data processor 23 processes the received data in order to determine the orientation angle θ of the wearable bladder monitoring device 1 relative to the abdomen of the subject 40. Specifically, the data processor 23 evaluates the respective echo signals 40 to identify the subset of echo signals 40 reflected by the pelvic bone 43, which echo signals may be identified as previously explained with the aid of FIG. 6, in order to identify the edge of the pelvic bone 43 proximal to the bladder 41 from this subset of echo signals 40. This echo signal for example may be identified by systematically evaluating the echo signals as a function of reducing beam angle of the ultrasound beams corresponding to these echo signals in order to find the ultrasound beam 30 with the lowest beam angle leading to an echo signal reflecting off the pelvic bone 43. Because the wearable bladder monitoring device 1 is positioned in an (approximately) fixed position relative to the pelvic bone 43, the relative orientation angle θ of the wearable bladder monitoring device 1 can be derived from this beam angle information by the data processor 23 in operation 111 of the method 100.

In operation 113, the data processor 23 fits the echo signals 31' of the ultrasound beams 30' passing through a section of the bladder 41 to a bladder model. In operation 115, the data processor 23 may estimate a diameter or cross-sectional length of the bladder section from the distance or time delay between the respective edges 33 and 33' of each echo signal 31' indicative of the anterior and posterior wall sections of the bladder 41 delimiting this bladder section. The positioning of the trajectory of the ultrasound beams 30' onto this bladder model may be based on the determined orientation angle θ, as well as the delay of edges 33 and 33', i.e. the depth of the bladder location, of the wearable bladder monitoring device 1, such that a distinction can be made between trajectories resulting from different orientation angles of the wearable bladder monitoring device 1, such as example orientation angles $\theta_1$ and $\theta_2$ as schematically depicted in FIG. 7.

Based on the trajectories fitted onto the bladder model and the respective diameters (cross-sectional lengths) of the bladder 41 along these respective trajectories, the data processor 23 may in operation 117 estimate a bladder volume of the bladder 41. This for example may be based on the number of ultrasound beams 30' and the respective beam angles of these beams as well as on a defined orientation of the bladder model relative to the pelvic bone 43, such that a portion of the bladder model obscured from the ultrasound beams 30 by the pelvic bone 43 as a function of the orientation angle θ of the wearable bladder monitoring device 1 can be estimated from the determined orientation angle θ. Consequently, the volume of the portion of the bladder 41 visible to the ultrasound beams 30' may be extrapolated to a total bladder volume in this manner.

In an embodiment, the wearable bladder monitoring device 1 may be adapted to periodically repeat the monitoring of the bladder at a defined monitoring or operating frequency such as to monitor changes in the bladder volume over the monitoring period. This for example may be used to determine a rate of change in the bladder volume, from which diagnostic observations may be derived, such as a rehydration or dehydration rate of the subject 40. Also, monitoring the bladder volume over a period of time may provide valuable insights into the retention volume of the bladder 41, which as previously explained is an indicator of prostate and urinary tract conditions, with the consequent bladder stretching being a key contributor to the occurrence of delirium in elderly subjects 40. In order to preserve the battery life of the battery 15, the defined monitoring frequency should be chosen as low as possible. In an embodiment, the data processor 23 is adapted to define the operating frequency from an evaluation of a previous bladder monitoring event or set of bladder monitoring events, e.g. based on a previously determined filling or emptying rate of the bladder 41 or on a suspected pathology of the bladder 41.

To this end, the data processor 23 periodically may send a monitoring instruction to the phased array controller 13 of the wearable bladder monitoring device 1 to trigger a monitoring event as described above, with the periodicity of the monitoring instructions corresponding to the desired operating frequency of the wearable bladder monitoring device 1. Alternatively, the data processor 23 may send a monitoring instruction to the phased array controller 13 of the wearable bladder monitoring device 1 in which the operating frequency is defined such that the phased array controller 13 autonomously can trigger monitoring events in accordance with the operating frequency specified in the received monitoring instruction. It will be understood that the communication of such monitoring instructions typically involves a communication between a system communication module 22 of the remote device 5 and the device communication module 21 of the wearable bladder monitoring device 1.

The method 100 optionally may further comprise the generation of a warning signal in operation 119 with the data processor 23, which warning signal for example may be generated as an audible or visible warning signal with the remote device 5 under control of the data processor 23. The data processor 23 may generate the warning signal in response to the estimation of a particular bladder volume or change in the bladder volume. Such a warning signal for example may be generated to wake a sleeping subject 40 in case of the bladder 41 of the subject 40 gets overly full, e.g. in order to prevent wetting of the subject's bed in case of incontinence. Alternatively, such a warning signal may be used to inform an athlete about his or her hydration levels, e.g. to ensure appropriate post-exercise rehydration. Alternatively, the warning signal may be generated by an alarming system connected to the remote data repository, which alarming system may be adapted to process the data uploaded into the remote data repository by the wearable bladder monitoring device 1 and to generate the warning signal based on said processing. The method 100 may subsequently terminate in operation 121.

Figure 9:
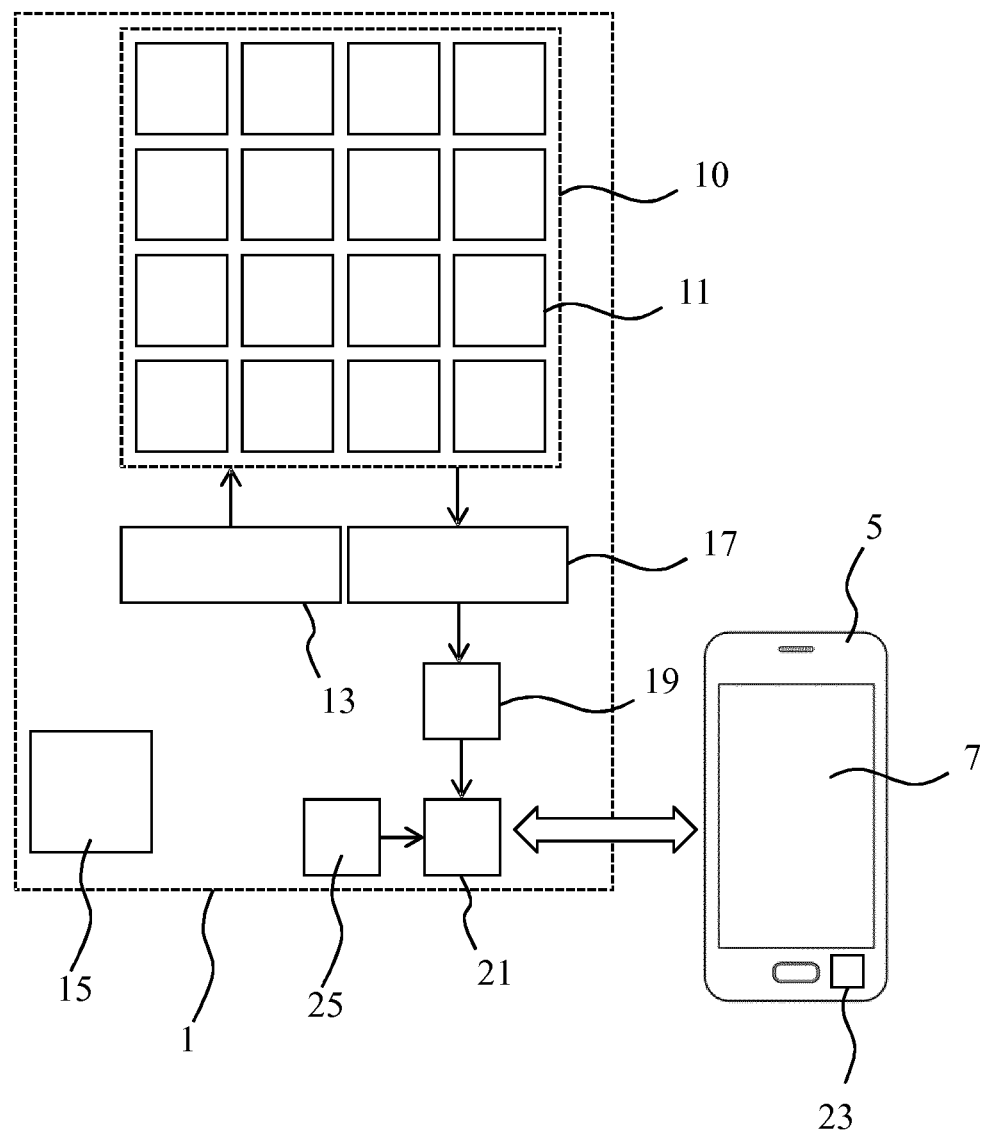
FIG. 9 schematically depicts a bladder monitoring system according to another embodiment.

In order to further refine the bladder volume estimation from the data pertaining to the echo signals generated with the wearable bladder monitoring device 1, this device may further comprise an orientation sensor 25 as schematically depicted in FIG. 9. Such an orientation sensor 25, e.g. an accelerometer or the like, is typically adapted to determine the orientation, e.g. posture or pose, of the subject 40, as different orientations of the subject 40 may lead to changes in the shape and position of the bladder 41. Therefore, by including the orientation data provided by the orientation sensor 25 in the data to be provided to the signal processor 23, the signal processor 23 may estimate the bladder volume of the bladder 41 of the subject 40 based on the combination of the data pertaining to the echo signals 31 of the ultrasound beams 30 and the orientation data provided by the orientation sensor 25.

In an embodiment, the signal processor 23 has access to a plurality of bladder models, e.g. stored in a data storage device (not shown), which may be contained by the device also containing the signal processor 23, e.g. the remote device 5 or the wearable bladder monitoring device 1, or may be a remote data storage device accessible over a network such as the Internet by the signal processor 23, e.g. through wireless communication module as will be readily understood by the skilled person. Each bladder model may be associated with a particular orientation (posture or pose) of the subject 40, such that the appropriate bladder model may be selected by the signal processor 23 based on the orientation data generated with the orientation sensor 25.

A further refinement of the accuracy of the bladder volume estimation may be obtained by optimizing the output or ultrasound frequencies of the ultrasound beams 30' passing through the bladder 41. This can be understood as follows. As previously explained, the echo signals 31' of the ultrasound beams 30' exhibit a pair of 'steep' intensity changes 33 and 33' corresponding to the ultrasound beam 30' passing through an anterior wall section and a posterior wall section respectively of the bladder 41. In order to accurately locate the respective positions of these anterior and posterior wall sections, this intensity change preferably should be as steep as possible, such that the distance over which this intensity change is spread is minimized, thereby minimizing the uncertainty in the exact locations of these wall sections and consequently improving the accuracy of the estimated distance, i.e. bladder diameter or cross-sectional length, between these wall sections.

Figure 10:
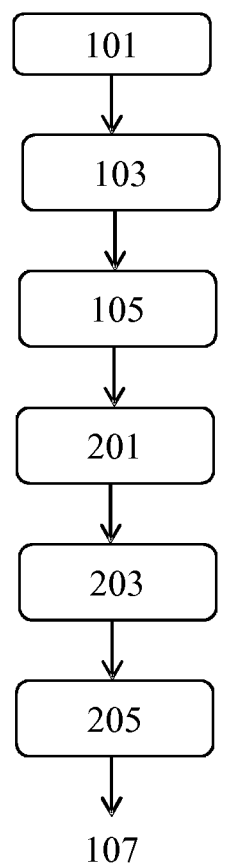
FIG. 10 is a flowchart of an aspect of another example embodiment of a method of monitoring a bladder with a bladder monitoring system according to an embodiment.

This may be achieved by tuning the frequency of the ultrasound beams 30' as a function of the actual depth and size of the bladder 41, as will be explained in further detail with the aid of FIG. 10, which depicts a flowchart of a refinement of the method 100 in which such frequency optimization is deployed. As is well-known per se, the ultrasound frequency is proportional to the image resolution and inversely proportional to the imaging depth. Hence, for a bladder 41 there exists an optimal ultrasound frequency f1 for the measurement of the anterior wall section of the bladder 41 as well as an optimal ultrasound frequency f2 for the measurement of the posterior wall section of the bladder 41, with typically f1≠f2 due to the different distances of the anterior and posterior wall sections from the abdominal surface of the subject 40.

Hence, in an embodiment the wearable bladder monitoring device 1 is adapted to tune the ultrasound frequency of the ultrasound beams 30', i.e. at least of the ultrasound beams passing through the bladder 41, in order to improve the accuracy of the anterior and posterior wall section localizations. To this end, in operation 103 the phased array controller 13 may control the phased array 10 to generate ultrasound beams at various beam angles at an initial frequency which initial frequency typically is a relatively low frequency, e.g. a frequency of about 2 MHz, in order to generate a relatively wide angle ultrasound beam and large penetration depth, with the echo signals induced by these ultrasound beams being acquired in operation 105 as previously explained. This enables the bladder monitoring system to roughly determine the position and size of the bladder 41 due to the wide angled nature of the low frequency ultrasound beam.

This rough estimation of the position and size of the bladder 41 is used in operation 201 to determine a first distance $d_a$ to the anterior wall of the bladder 41 and a second distance $d_b$ to the posterior wall of the bladder 41, which distances in combination with the attenuation rate of ultrasound waves in fat tissue, e.g. about 0.5 dB/MHz/cm, to determine an optimal ultrasound frequencies f1 and f2 for imaging the anterior and posterior walls of the bladder 41, e.g. using the formula f=M/(0.5*D), in which f is the optimal ultrasound frequency, M is the maximum attenuation threshold for the signal to noise ratio specific phased array 10 and D is the distance to the wall section to be imaged.

Subsequently, the bladder 41 may be imaged in operation 203 with ultrasound signals at the determined optimal ultrasound frequencies f1 and f2 with the respective echoes of these ultrasound signals being acquired in operation 205 such that the bladder volume estimation with the signal processor 23 may be based on the echo signals of the ultrasound beams at the optimal ultrasound frequencies f1 and f2 in order to improve the accuracy of the bladder volume estimation. This for example may be achieved by combining the ultrasound beams at the optimized frequencies under various beam angles as previously explained into a single evaluation, e.g. by mapping the echo signals of these ultrasound beams onto a bladder model as previously explained. Alternatively, rather than performing multiple ultrasound measurements at the respective optimal ultrasound frequencies f1 and f2, a single measurement (scan) may be performed at an ultrasound frequency that is an average of the optimal ultrasound frequencies f1 and f2, e.g.

a weighted average at 110% of the optimal ultrasound frequency f2 for imaging the posterior wall sections, as f2 typically is lower than f1.

Figure 8:
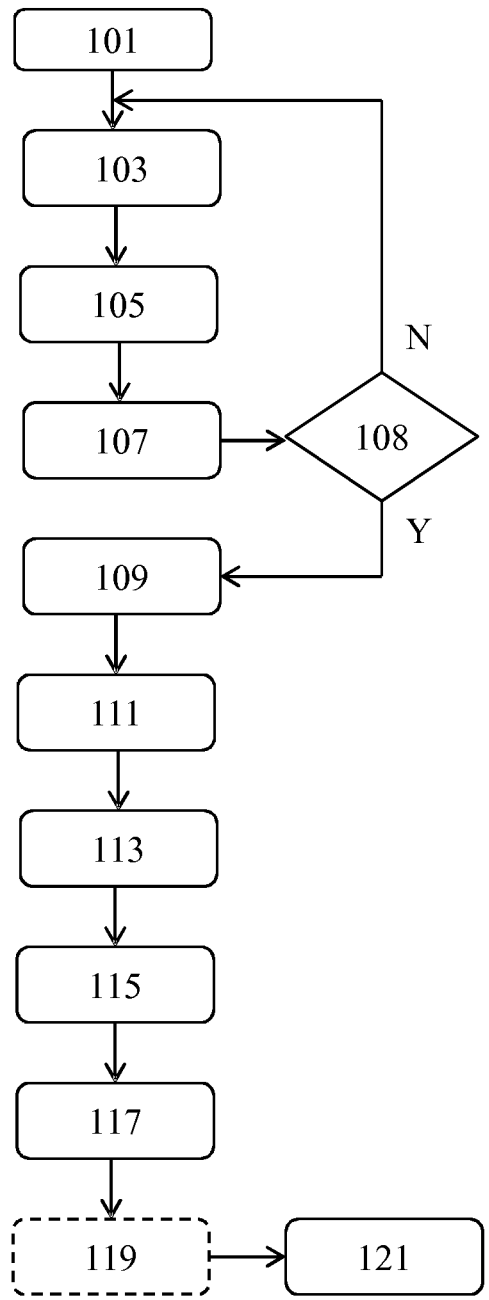
FIG. 8 is a flowchart of an example embodiment of a method of monitoring a bladder with a bladder monitoring system according to an embodiment.

As previously explained, the acquired echo signals may be pre-processed in operation 107 and further processed as explained in more detail with the aid of the flowchart of FIG. 8. It is noted that where such frequency optimization of the ultrasound beams is to be included in the operation of the wearable bladder monitoring device 1, the ultrasound transducer elements 11 preferably are CMUT elements due to their superior bandwidth characteristics compared to e.g. PZT elements.

Figure 11:
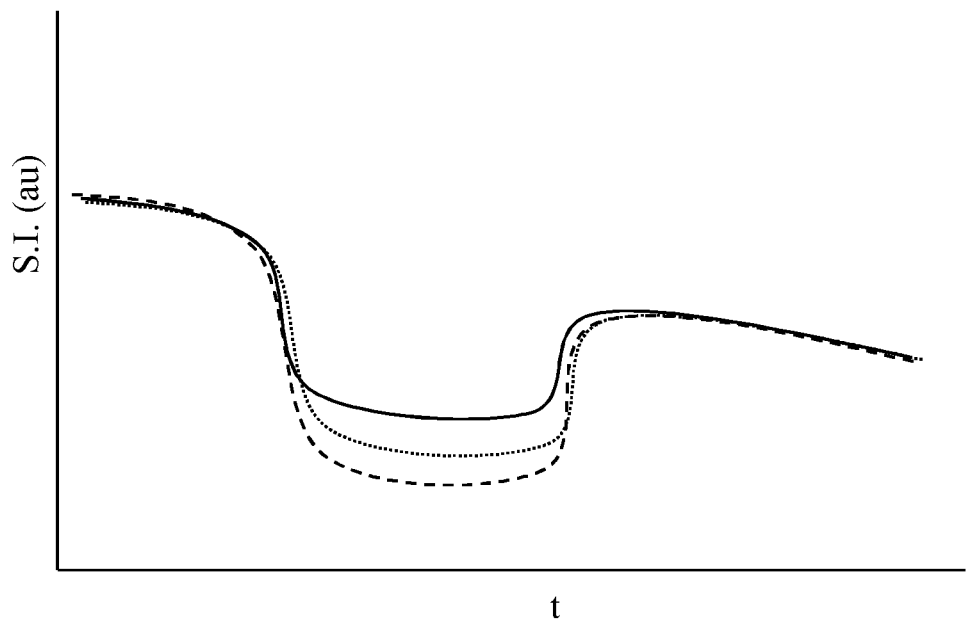
FIG. 11 schematically depicts the attenuation of an echo signal of an ultrasound beam passing through a bladder for different degrees of turbidity of the urine contained in the bladder.

In embodiments of the present invention, the data processor 23 is further arranged to optimize the output or ultrasound frequencies of the ultrasound beams 30' for the purpose of monitoring the degree of turbidity of urine contained in the bladder 41 of the subject 40. FIG. 11 schematically depicts differently attenuated echo signals of an ultrasound beam 30' passing through the bladder 41, which attenuations are a function of the amount of urine in the bladder 41, i.e. of the volume of the bladder 41, as this volume is determined by the amount of urine therein, as is well-known per se. Therefore, the attenuation strength of these echo signals can be used to estimate a degree of turbidity of the urine within the bladder 41.

In order to facilitate the accurate determination of the degree of turbidity of the urine contained in the bladder 41, the attenuation of these echo signals should be optimized, as will be readily understood by the skilled person. Such optimization may be achieved by calculating the optimal ultrasound frequencies f1 and f2 (or their weighted average as previously explained) based on the data pertaining to the initially obtained echo signals from the phased array 10 of the wearable bladder monitoring device 1 for each beam angle under which an ultrasound beam 30' passes through a section of the bladder 41 as previously explained. As will be explained in further detail below, such a set of optimal ultrasound frequencies for the ultrasound beams to be generated under a particular beam angle is not necessarily limited to one or two optimal frequencies but may include additional ultrasound frequencies, e.g. to capture a frequency dependency of the attenuation of the echo signals from such ultrasound beams. In an embodiment, a single beam angle is selected by the data processor 23 for such an optimized urine turbidity determination, e.g. the beam angle corresponding to the longest path of an ultrasound beam 30' through the bladder 41.

The data processor 23 may determine the set of optimal frequencies for the respective beam angles from the bladder volume and its position relative to the wearable bladder monitoring device 1 as previously explained and generate a configuration instruction for the phased array controller 13 including the determined set of optimal frequencies, which configuration instruction may be relayed to the device communication module 21 of the wearable bladder monitoring device 1 through the system communication module 22 of the remote device 5 under control of the data processor 23. Such a configuration instruction typically comprises a set of output or ultrasound frequencies for each beam angle under which the ultrasound beams 30' having these output or ultrasound frequencies are travelling through a section of the bladder 41.

The respective sets of output or ultrasound frequencies for the different beam angles may be identical, although in a preferred embodiment different sets of output or ultrasound frequencies are defined for different beam angles such that each set of ultrasound beams 30' generated under that particular beam angle under control of the phased array controller 13 has its individually optimized set of output or ultrasound frequencies. The phased array controller 13 typically is configured by the configuration instruction such that the phased array controller 13 controls the phased array 10 of ultrasound transducer 11 to generate the respective sets of ultrasound beams 30' under each discrete beam angle for which the ultrasound beams 30' pass through the bladder 41, e.g. a single beam angle or a plurality of beam angles, with each ultrasound beam in such a set being configured to have one of the output ultrasound frequencies as defined by the data processor 23, wherein in case of a plurality of ultrasound beams 31' being generated for a particular beam angle in this manner, different ultrasound beams 31' will have different output or ultrasound frequencies as will be readily understood from the foregoing. Alternatively, an ultrasound beam with a (substantially) continually varying output or ultrasound frequency may be generated, in which case the ultrasound beam implements a form of ultrasound spectroscopy in which a spectrum of ultrasound frequencies is applied to the bladder 41 under the chosen beam angle.

Figure 12:
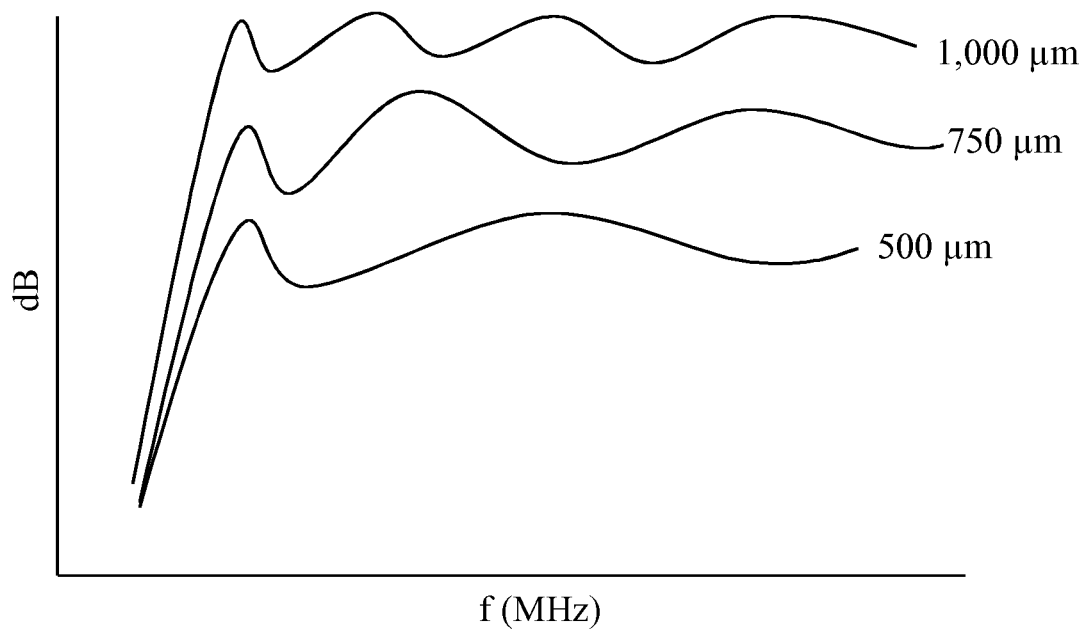
FIG. 12 schematically depicts the attenuation of an echo signal of an ultrasound beam passing through a bladder as a function of particle size and ultrasound frequency.
Figure 13:
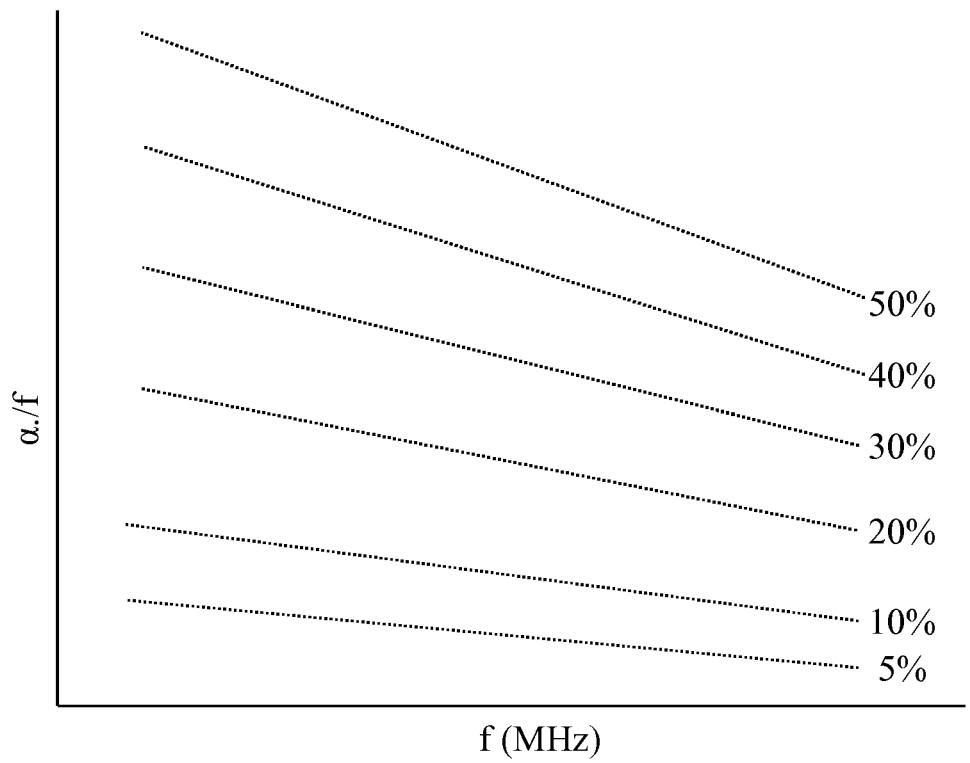
FIG. 13 schematically depicts the attenuation of an echo signal of an ultrasound beam passing through a bladder as a function of particle concentration and ultrasound frequency.

In an embodiment, the echo signals of the thus generated one or more sets of ultrasound beams 31' may be pre-processed by the down conversion stage 17 and subsequently transmitted to the remote device 5 through the device communication module 21, where the data pertaining to these pre-processed echo signals may be processed by the data processor 23 to determine the degree of turbidity of the urine within the bladder 41 from the attenuation strength of these echo signals.

Where multiple ultrasound beams 30' having different output or ultrasound frequencies are transmitted through the bladder 41 under a discrete beam angle, the data processor 23 may be further adapted to determine at least one of a particle size and a particle concentration of a substance causing the turbidity of the urine contained within the bladder 41. This will be explained in more detail with the aid of FIG. 12, which schematically depicts the attenuation of an echo signal 31' as a function of the frequency f of its ultrasound beam 30' and the particle size of such a substance in the urine contained within the bladder 41 (three curves for particle sizes 500 µm, 750 µm and 1,000 µm are shown by way of non-limiting example) and FIG. 13, which schematically depicts the attenuation of an echo signal 31' as a function of the frequency f of its ultrasound beam 30' and the particle concentration of such a substance in the urine contained within the bladder 41 (six curves for particle concentrations 5%, 10%, 20%, 30%, 40% and 50%, all by weight, are shown by way of non-limiting example).

Using calibration data, e.g. provided in calibration tables or calibration functions, the data processor 23 may be adapted to match the frequency-dependent attenuation of the echo signals received from the wearable bladder monitoring device 1 to a particular particle size and/or concentration as defined by the calibration data, such that in a particular advantageous embodiment the type of substance clouding the urine can be determined from such frequency-dependent attenuation behaviour of the echo signals. This is because different types of substances typically exhibit different typical particle sizes or particle size distributions such that the frequency-dependent attenuation behaviour may be used to distinguish between different types of particles such as white blood cells, red blood cells or chyle. The ability to distinguish between such different types of particles may provide important clinical information about the subject 40, in particular about urinary tract conditions from which the subject 40 may be suffering or the onset of such conditions, as (the onset of) different urinary tract conditions may be characterised by different types of substances clouding the urine contained in the bladder 41 of the subject 40. Moreover, various diseases such as kidney disorders, liver disorders, diabetes or other metabolic conditions influence the degree of turbidity and the types of particles causing such turbidity of the urine in the bladder 41, which diseases may be diagnosed with the aid of the turbidity information obtained as explained above.

The remote device 5 may be configured to communicate the degree of turbidity of the urine contained within the bladder 41 and optionally type of substance clouding the urine to its user in any suitable manner. In a straightforward implementation, the data processor 23 may be configured to control a display of the remote device 5 such that these results are displayed on this display although other suitable ways of communication of such results to the user with the remote device 5 will be immediately apparent to the skilled person.

In an embodiment, the data processor 23 is configured to generate the configuration instruction for generating the urine turbidity data with the phased array 10 of the wearable bladder monitoring device 1 in response to the estimated bladder volume of the bladder 41 having reached at least matching a defined minimum value. This ensures that the degree of turbidity of the urine contained within the bladder 41 is only determined when the bladder 41 is sufficiently full to minimize the risk of an inaccurate estimation of the degree of turbidity due to insufficient urine being contained by the bladder 41. However, in an alternative embodiment the data processor 23 is configured to periodically generate such a configuration instruction, the periodicity of which may be defined such that there is sufficient time between successive configuration instructions for the bladder 41 to sufficiently fill with urine. In yet another embodiment, such turbidity measurements, i.e. the generation of the configuration instructions with the data processor 23 triggering the configuration of the phased array controller 13 as previously explained, is based on rate of change of the bladder volume, e.g. a filling or emptying rate of the bladder 41. In a further embodiment, such periodic measurements are used to monitor changes in the degree of turbidity of the urine contained by the bladder 41 of the subject 40 with the data processor 23, which changes in the degree of turbidity may also provide clinically relevant information regarding particular diseases or their onset.

The above described embodiments of the methods of the present invention may be realized by computer readable program instructions embodied on a computer readable storage medium having, when executed on the data processor 23, cause the data processor 23 to implement such a method. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on. The computer readable storage medium may be a medium that is accessible over a network such as the Internet, such that the computer readable program instructions may be accessed over the network. For example, the computer readable storage medium may be a network-attached storage device, a storage area network, cloud storage or the like. The computer readable storage medium may be an Internet-accessible service from which the computer readable program instructions may be obtained. In an embodiment, the remote device 5 is adapted to retrieve the computer readable program instructions from such a computer readable storage medium and to create a new computer readable storage medium by storing the retrieved computer readable program instructions in a data storage arrangement, e.g. in a memory device or the like forming part of the remote device 5.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A bladder monitoring system for processing data pertaining to echo signals from a wearable bladder monitoring device comprising:
    a fastener adapted to secure the wearable bladder monitoring device to a subject's body;
    a phased array of ultrasound transducers having configurable output frequencies;
    a configurable phased array controller adapted to control the phased array of ultrasound transducers to direct ultrasound beams into the subject's body under a plurality of discrete beam angles and to collect echo signals of the ultrasound beams, wherein the configurable phased array controller is adapted to direct a set of ultrasound beams into the subject's body for at least a subset of the discrete beam angles in response to a configuration instruction defining the respective output frequencies of the ultrasound beams in the set of ultrasound beams; and
    a device transceiver adapted to communicate data pertaining to the echo signals;
    the bladder monitoring system comprising:
    a system transceiver adapted to communicate data pertaining to echo signals from the device transceiver of the wearable bladder monitoring device; and
    a data processor communicatively coupled to the system transceiver and adapted to process the data pertaining to the echo signals to:
    identify an edge of a subject's pelvic bone proximal to a subject's bladder from data pertaining to at least one of the echo signals;
    determine an orientation of the wearable bladder monitoring device relative to the pelvic bone based on beam angle information associated with the at least one of the echo signals; and
    derive bladder information from the data based on the determined orientation; the data processor further being arranged to:
    generate the configuration instruction defining a set of output frequencies for at least a subset of the discrete beam angles based on defined bladder information for determining a degree of turbidity of urine contained in the subject's bladder; and control the system transceiver to communicate the configuration instruction to the device transceiver of the wearable bladder monitoring device.

2. The bladder monitoring system of claim 1, further comprising the wearable bladder monitoring device.

3. The bladder monitoring system of claim 2, wherein the configurable phased array controller is further configurable to operate the phased array of ultrasound transducers at an operating frequency defined by a monitoring instruction received through the device transceiver.

4. The bladder monitoring system of claim 2, wherein the device transceiver comprises a wireless communication transceiver.

5. The bladder monitoring system of claim 2, wherein the fastener comprises a strap attached to the wearable bladder monitoring device or an adhesive layer on a subject-facing surface of the wearable bladder monitoring device.

6. The bladder monitoring system of claim 1, wherein the set of ultrasound frequencies comprises a first set of ultrasound frequencies for a first discrete beam angle in the subset, and a second set of ultrasound frequencies for a second discrete beam angle in the subset.

7. The bladder monitoring system of claim 1, wherein the data processor is further adapted to determine the degree of turbidity of urine from the data pertaining to the echo signals of the set of ultrasound beams.

8. The bladder monitoring system of claim 7, wherein the data processor is adapted to determine at least one of a type of a substance and a concentration of a substance in urine contained in the bladder of the subject based on a frequency-dependent attenuation of the echo signals of the set of ultrasound beams.

9. The bladder monitoring system of claim 1, wherein the data processor is adapted to estimate a diameter of the subject's bladder for each echo signal from the data pertaining to the echo signals of the ultrasound beams and to estimate a bladder volume by fitting the estimated diameters of the subject's bladder to a defined bladder model and estimating the bladder volume from a fitting result.

10. The bladder monitoring system of claim 9, wherein the data processor is adapted to generate the configuration instruction in response to the estimated bladder volume at least matching a defined minimum value.

11. The bladder monitoring system of claim 1, wherein the data processor further is adapted to define an operating frequency of the wearable bladder monitoring device based on a change in estimated bladder volume over time and to generate a monitoring instruction for the wearable bladder monitoring device based on the defined operating frequency.

12. A computer-implemented method for determining a degree of turbidity of urine contained in a bladder of a subject monitored with a wearable bladder monitoring device comprising:
a fastener adapted to secure the wearable bladder monitoring device to a subject's body;
a phased array of ultrasound transducers having configurable output frequencies;
a configurable phased array controller adapted to control the phased array of ultrasound transducers to direct ultrasound beams into the subject's body under a plurality of discrete beam angles and to collect echo signals of the ultrasound beams, wherein the configurable phased array controller is adapted to direct a set of ultrasound beams into the subject's body for at least a subset of the discrete beam angles in response to a configuration instruction defining the respective output frequencies of the ultrasound beams in the set of ultrasound beams; and
a device transceiver adapted to communicate data pertaining to the echo signals of the ultrasound beams; the method comprising:
receiving the data pertaining to the echo signals from the device transceiver;
processing the data pertaining to the echo signals to:
identify an edge of a subject's pelvic bone proximal to a subject's bladder from data pertaining to at least one of the echo signals;
determine an orientation of the wearable bladder monitoring device relative to the pelvic bone based on beam angle information associated with the at least one of the echo signals; and
derive bladder information from the data based on the determined orientation;
generating a configuration instruction defining a set of output frequencies for at least a subset of the discrete beam angles based on defined bladder information for determining a degree of turbidity of urine contained in the bladder, the configuration instruction causing the configurable phased array controller to generate the set of ultrasound beams each having a defined output frequency of the set of output frequencies for each of the discrete beam angles in the subset; and
communicating the configuration instruction to the device transceiver.

13. The computer-implemented method of claim 12, further comprising determining the degree of turbidity from the data pertaining to the echo signals of the set of ultrasound beams.

14. The computer-implemented method of claim 13, further comprising determining at least one of a type of at least one substance and a concentration of at least one substance in the urine contained in the bladder of the subject based on a frequency-dependent attenuation of the echo signals of the set of ultrasound beams.

15. A non-transitory computer readable medium that stores instructions, which when executed by a processor, cause the processor to:
process received data pertaining to echo signals from a device transceiver to:
identify an edge of a subject's pelvic bone proximal to a subject's bladder from data pertaining to at least one echo signal;
determine an orientation of a wearable bladder monitoring device relative to a pelvic bone based on beam angle information associated with the at least one echo signal; and
derive bladder information from the data based on the determined orientation;
generate a configuration instruction defining a set of output frequencies for at least a subset of discrete beam angles based on defined bladder information for determining a degree of turbidity of urine contained in the bladder, the configuration instruction causing a configurable phased array controller to generate a set of ultrasound beams each having a defined output frequency of the set of output frequencies for each of the discrete beam angles in the subset of discrete beam angles; and
communicate the configuration instruction to the device transceiver.

16. The non-transitory computer readable medium of claim 15, wherein the instructions, which when executed by a processor, further cause the processor to determine the degree of turbidity from the data pertaining to the echo signals of the set of ultrasound beams.

17. The non-transitory computer readable medium of claim 15, wherein the instructions, which when executed by a processor, further cause the processor to determine at least one of a type of at least one substance and a concentration of at least one substance in the urine contained in the bladder of a subject based on a frequency-dependent attenuation of the echo signals of the set of ultrasound beams.

18. The non-transitory computer readable medium of claim 15, wherein the instructions, which when executed by a processor, further cause the processor to determine at least one of a type of a substance and a concentration of a substance in the urine contained in the bladder of a subject based on a frequency-dependent attenuation of the echo signals of the set of ultrasound beams.

19. The non-transitory computer readable medium of claim 15, wherein the instructions, which when executed by a processor, further cause the processor to estimate a diameter of a subject's bladder for each echo signal from the data pertaining to the echo signals of the ultrasound beams and to estimate a bladder volume by fitting the estimated diameters of the subject's bladder to a defined bladder model and estimating the bladder volume from a fitting result.

20. The non-transitory computer readable medium of claim 19, wherein the instructions, which when executed by a processor, further cause the processor to generate the configuration instruction in response to the estimated bladder volume at least matching a defined minimum value.

* * * * *